(12) United States Patent
Deitcher

(10) Patent No.: US 11,701,392 B2
(45) Date of Patent: *Jul. 18, 2023

(54) COMPOSITIONS FOR ESTABLISHING MIXED CHIMERISM AND METHODS OF MANUFACTURE THEREOF

(71) Applicant: MEDEOR THERAPEUTICS, INC., South San Francisco, CA (US)

(72) Inventor: Steven R. Deitcher, San Mateo, CA (US)

(73) Assignee: MEDEOR THERAPEUTICS, INC., South San Francisco, CA (US)

( * ) Notice: Subject to any disclaimer, the term of this patent is extended or adjusted under 35 U.S.C. 154(b) by 276 days.

This patent is subject to a terminal disclaimer.

(21) Appl. No.: 17/104,011

(22) Filed: Nov. 25, 2020

(65) Prior Publication Data

US 2021/0077534 A1 Mar. 18, 2021

Related U.S. Application Data

(63) Continuation of application No. 15/946,099, filed on Apr. 5, 2018, now Pat. No. 10,881,692.

(51) Int. Cl.
*A61K 35/28* (2015.01)

(52) U.S. Cl.
CPC .................. *A61K 35/28* (2013.01)

(58) Field of Classification Search
None
See application file for complete search history.

(56) References Cited

U.S. PATENT DOCUMENTS

| | | | |
|---|---|---|---|
| 5,607,579 A | 3/1997 | Latham, Jr. et al. |
| 5,772,994 A | 6/1998 | Ildstad et al. |
| 5,876,708 A | 3/1999 | Sachs |
| 6,280,957 B1 | 8/2001 | Sayegh et al. |
| 6,544,506 B2 | 4/2003 | Reisner |
| 6,558,662 B2 | 5/2003 | Sykes et al. |
| 6,743,192 B1 | 6/2004 | Sakota et al. |
| 6,877,514 B2 | 4/2005 | Sykes |
| 7,270,810 B2 | 9/2007 | Reisner et al. |
| 7,288,255 B1 | 10/2007 | Shlomchik et al. |
| 7,297,329 B2 | 11/2007 | Akashi et al. |
| 7,332,157 B2 | 2/2008 | Sykes |
| 7,638,121 B2 | 12/2009 | Sykes |
| 7,776,591 B2 | 8/2010 | Xia et al. |
| 7,811,815 B2 | 10/2010 | Brown |
| 7,939,062 B2 | 5/2011 | Sykes |
| 8,632,768 B2 | 1/2014 | Ildstad et al. |
| 8,734,786 B2 | 5/2014 | Miller et al. |
| 8,916,147 B2 | 12/2014 | Reisner |
| 8,980,329 B2 | 3/2015 | Brown |
| 9,090,871 B2 | 7/2015 | Durrant et al. |
| 9,364,600 B2 | 6/2016 | Pages et al. |
| 9,452,184 B2 | 9/2016 | Ildstad et al. |
| 9,504,717 B2 | 11/2016 | Strober et al. |
| 9,545,427 B2 | 1/2017 | Brown |
| 9,561,253 B2 | 2/2017 | Strober et al. |
| 9,678,062 B2 | 6/2017 | Ildstad et al. |
| 9,695,394 B1 | 7/2017 | Coelho et al. |
| 10,603,340 B2 | 3/2020 | Strober et al. |
| 11,435,350 B2 | 9/2022 | Zdanowski et al. |
| 2002/0107469 A1 | 8/2002 | Bolan et al. |
| 2008/0199949 A1 | 8/2008 | Alroy |
| 2010/0042015 A1 | 2/2010 | Brown |
| 2010/0310588 A1 | 12/2010 | Bluestone et al. |
| 2011/0110909 A1 | 5/2011 | Ildstad et al. |
| 2012/0177621 A1 | 7/2012 | Strober et al. |
| 2012/0329668 A1 | 12/2012 | Sarwal et al. |
| 2014/0004085 A1 | 1/2014 | Kaplan |
| 2014/0369974 A1 | 12/2014 | Reisner et al. |
| 2016/0046974 A1 | 2/2016 | Efcavitch et al. |
| 2017/0106086 A1 | 4/2017 | Strober et al. |
| 2018/0221410 A1 | 8/2018 | Strober et al. |
| 2019/0225940 A1 | 7/2019 | Vo et al. |
| 2019/0358269 A1 | 11/2019 | Reisner et al. |
| 2021/0189344 A1 | 6/2021 | Veale et al. |

FOREIGN PATENT DOCUMENTS

| | | |
|---|---|---|
| EP | 2606120 B1 | 10/2015 |
| WO | 1995003062 A1 | 2/1995 |
| WO | 2002040640 A2 | 5/2002 |
| WO | 2003012060 A2 | 2/2003 |
| WO | 03101201 A1 | 12/2003 |
| WO | 2011068829 A1 | 6/2011 |
| WO | 2012024427 A2 | 2/2012 |
| WO | 2012096974 A1 | 7/2012 |
| WO | 2013093919 A2 | 6/2013 |
| WO | 2014133729 A1 | 9/2014 |

(Continued)

OTHER PUBLICATIONS

Alexander, 2008, Chimerism and Tolerance in a Recipient of a Deceased-Donor Liver Transplant, N Engl J Med, 358:369-74.

Arai, 2015, Increasing Incidence of Chronic Graft-versus-Host Disease in Allogeneic Transplantation: A Report from the Center for International Blood and Marrow Transplant Research, Biol Blood Marrow Transplant, 21:266-274.

Arbab, 2004, Efficient Magnetic Cell Labeling with Protamine Sulfate Complexed to Ferumoxides for Cellular MRI Blood, American Soc. of Hematology, 104(4):1217-1223.

Bakhuraysah, 2016, Hematopoietic stem cell transplantation for multiple sclerosis: is it a clinical reality? Sem Cell Res Ther. 2016; 7:12, 12 pages.

(Continued)

*Primary Examiner* — Michelle F. Paguio Frising

(74) *Attorney, Agent, or Firm* — Brown Rudnick LLP; Adam M. Schoen

(57) ABSTRACT

The invention provides compositions for establishing mixed chimerism in a subject. The compositions include $CD34^+$ cells that have been column-purified from an apheresis product and $CD3^+$ cells from an apheresis product that have not been purified through a column. The invention also provides methods of making and using such compositions.

20 Claims, No Drawings

(56) References Cited

FOREIGN PATENT DOCUMENTS

| WO | 2015/172080 A1 | 11/2015 |
|---|---|---|
| WO | 2016/201111 A1 | 12/2016 |
| WO | 2017/005647 A1 | 1/2017 |

OTHER PUBLICATIONS

Beelen, 2000, Transplantation of highly purified HLA-identical sibling donor peripheral blood CD34+ cells without prophylactic post-transplant immunosuppression in adult patients with first chronic phase chronic myeloid leukemia: results of a phase II study, Bone Marrow Transplantation, 823-829, 26, Macmillan Publishers Ltd., Basingstoke, United Kingdom.

Dick, 1997, Assay of human stem cells by repopulation of NOD/SCID mice, Stem Cells, 1997;15 Suppl 1:199-203.

Field, 2001, Tolerance, mixed chimerism and protection against graft-versus-host disease after total lymphoid irradiation, Phil. Trans. R. Soc. Lond. B, 356:739-748.

Frisch, 2014, Hematopoietic Stem Cell Cultures and Assays, Methods Mol Biol. 2014; 1130: 315-324.

Fudaba, 2006, Myeloma Responses and Tolerance Following Combined Kidney and Nonmyeloablative Marrow Transplantation: In Vivo and In Vitro Analyses, American Journal of Transplantation, 6: 2121-2133.

International Search Report and Written Opinion for International Application No. PCT/US2019/025958, filed Apr. 5, 2019, dated Jul. 2, 2019, 7 pages.

International Search Report and Written Opinion for International Application No. PCT/US2019/051711, filed Sep. 18, 2019, dated Jan. 15, 2020, 9 pages.

Jun. 2007, Adoptive T cell therapy for cancer in clinic, J Clin Invest, 117(6):1466-76, vol. 117.

Kalwak, 2010, Higher CD34+ and CD3+ Cell Doses in the Graft Promote Long-Term Survival, and Have No Impact in the Incidence of Severe Acute or Chronic Graft-versus-Host Disease after In Vivo T Cell-Depleted Unrelated Donor Hematopoietic Stem Cell Transplantation in Children, Biol Blood Marrow Transplant, 16:1388-1401.

Kawai, 2008, HLA-mismatched Renal Transplantation without Maintenance Immunosuppression, New England Journal of Medicine, 358(4):353-361.

Khalil, 2017, Rubbing Against Blood Clots Uding Helical Robots: Modeling and In Vitro Experimental Validation, IEEE Robotics and Automation Letter vol. 2, No. 2, 927-934.

Kohrt, 2009, TLI and ATG Conditioning with Low Risk of Graft-Versus-Host Disease Retains Antitumor Reactions after Allogeneic Hematopoietic Cell Transplantation from Related and Unrelated Donors, Blood, 114(5):1099-1109.

Ledford, 2008, Organ Transplant without Rejection, Nature News, ISSN 0028-0836, EISSN 1476-4687 (3 pages).

Leventhal, 2012, Chimerism and tolerance without GVHD or engraftment syndrome in HLA-mismatched combined kidney and hematopoietic stem cell transplantation, Sci Transl Med. 4(124):1-22.

Leventhal, 2013, Tolerance Induction in HLA Disparate Living Donor Kidney Transplantation by Donor Stem Cell Infusion: durable chimerism predicts outcome, Transplantation, 95(1):169-176.

Mali, 2013, Delivery systems for gene therapy, Indian J Hum Genet. Jan.-Mar. 2013; 19(1): 3-8, 8 pages.

Millan, 2002, Mixed chimerism and immunosuppressive drug withdrawal after HLA-mismatched kidney and hematopoietic progenitor transplantation, Transplantation, 73:1386-1391.

Ng, 2009, Isolation of human and mouse hematopoietic stem cells, Methods Mol Biol., 506:13-21.

Perez-Pujol, 2005, Proteomic analysis of gray platelet syndrome by iTRAQ Labelling and mass spetroscopy: a potential new diagnostic strategy for platelet disorders, Blood, (ASH Annual Meeting Abstracts), 106(11):2161.

Sachs, 2014,Induction of Tolerance through Mixed Chimerism, Cold Spring Harb Perspect Med, 4;4:a015529, 19 pages.

Scandling, 2008, Tolerance and Chimerism after Renal and Hematopoietic-Cell Transplantation, N Engl J Med, 358:362-8.

Scandling, 2012, Tolerance and withdrawal of immunosuppressive drugs in patients given kidney and hematopoietic cell transplants, Am J Transplant., 12(5):1133-45.

Scandling, 2015, Chimerism, Graft Survival, and Withdrawal of Immunosuppressive Drugs in HLA Matched and Mismatched Patients After Living Donor Kidney and Hematopoietic Cell Transplantation, American Journal of Transplantation, 15:695-704.

Slavin, 1977, Induction of specific tissue transplantation tolerance using fractionated total lymphoid irradiation in adult mice: long-term survival of allogeneic bone marrow and skin grafts, J. Exp. Med., 146:34-48.

Spohn, 2015, Automated CD34+ cell isolation of peripheral blood stem cell apheresis product, Cytotherapy, 10:1465-71.

Stanford Team Prevent Kidney Transplant Rejection Without Drugs, ScienceDaily, Apr. 24, 2002, pp. 1-3, downloaded from www.sciencedaily.com/releases/2002/04/020424072642.htm.

Strober, 2011, Translational studies in hematopoietic cell transplantation: treatment of hematologic malignancies as a stepping stone to tolerance induction, Semin Immunol., 23(4):273-81.

Sykes, 2001, Mixed Chimerism and Transplant Tolerance, Immunity, 14:417-424.

Szabolcs, 2012, Tolerance after solid organ and hematopoietic cell transplantation, Biol Blood Marrow Transplant, 18(1):S193-200.

Tatekawa, 2006, A novel direct competitive repopulation assay for human hematopoietic stem cells using NOD/SCID mice, Cytotherapy, vol. 8, No. 4, 390-398.

Urbano-Ispizua, 2001, The number of donor CD3+ cells is the most important factor for graft failure after allogeneic transplantation of CD34+ selected cells from peripheral blood from HLA-identical siblings, Blood,97(2):383-387.

Acenocoumarol from Wikipedia, the free encyclopedia pp. 1-3, downloaded Sep. 26, 2022.

Ades, 1989, Cell suspension from collagenase digestion of bone matton trephine biopsy specimens, Journal of Clinical Pathology, 42:427-432.

Aldenhoven, 2017, Quality of life of Hurler syndrome patients after successful hematopoietic stem cell transplantation, Blood Adv, 1(24):2236-2242.

Arber, 2016, The 2016 revision to the World Health Organization classification of myeloid neoplasms and acute leukemia. Blood, 127(20):2391-2405.

Bagul, 2008, Experimental renal preservation by normothermic resuscitation perfusion with autologous blood, British Journal of Surgery, 95:111-118.

Bennett, 2009, Diagnositc criteria to distinguish hypocellular acute myeloid leukemia from hypocellular myelodysplastic syndromes and aplastic anemia: recommendations for a standardized approach, Haematologica 94(2):264-268.

Bone marrow examination from Wikipedia, the free encyclopedia, pp. 1-5, downloaded Sep. 27, 2022.

Camitta, 1975, Selection of patients for bone marrrow transplantation in severe aplastic anemia, Blood 45(3):355-363.

Czerw, 2016, High CD3+ and CD34+ peripheral blood stem cell grafts content is associated with increased risk of graft-versus-host disease without beneficial effect on disease control after reduced-intensity conditioning allogeneic transplantation from matched unrelated donors for acute myeloid leukemia, Oncotarget, 7(19):27255-27266.

Extended European Search Report issued in European Application No. 19781109.4, dated Feb. 17, 2022, 6 pages.

Extended European Search Report issued in European Application No. 19782310.7, dated Feb. 17, 2022, 7 pages.

Extended European Search Report issued in European Application No. 19861568.4, dated Jun. 1, 2022, 7 pages.

Extended European Search Report issued in European Application No. 20748810.7, dated Oct. 20, 2022, 10 pages.

Greenberg, 2016, Cytopenia levels for aiding establishment of the diagnosis of myelodysplastic syndromes, Blood, 128(16):2096-2097.

(56) References Cited

OTHER PUBLICATIONS

Heparin from Wikipedia, the free encyclopedia, pp. 1-12, downloaded on Sep. 26, 2022.
Hildebrandt, 2000, Immunomagnetic selection of CD34 + cells: factors influencing component purity and yield, Transfusion, 40:507-512.
Kaloutsi, 1994, Comparison of Bone Marrow and Hematologic Findings in Patients with Human Immunodeficiency Virus Infection and Those with Myelody splastic Syndromes and Infectious Diseases, American Journal of Clinical Pathology, 101(2):123-129.
Levesque, 2008, Mobilization of hematopietic stem cells: Current Opinion in Organ Transplantation 13:53-58.
Link, 1995, Combined transplantation of allogeneic bone marrow and CD34+ blood cells, Blood 86(7):2500-2508.
Machalinski, 2003, An optimization of isolation of early hematopoietic cells from heparinized cadaveric organ donors, Transplantation Proceedings 35:3096-3100.
Marsh, 2009, Guidelines for the diagnosis and management of aplastic anaemia, Br J Haematol 147(1):43-70.
Mathew, 1998, Cellular immune responses of human cadaver donor bone marrow cells and their susceptibility to commonly used immunosuppressive drugs in transplantation, Transplantation, 66(7):947-955.
Merriam-Webster, definition for "exsanguination", retrieved from internet Sep. 23, 2022.
Monroy, 1987, The effect of recombinant GM-CSF in the recovery of monkeys transplanted with autologous bone marrow, Blood 70(5):1696-1699.
Montane, 2008, Epidemiology of aplastic anemia: a prospectice multicenter study, Haematologica, 93(4):518-523.
Reddy, 2021, Therapeutic Apheresis in Transfusion Medicine, J McCullough (Ed.) https://doi.org/10.1002/9781119599586.ch20 Chapter 20, pp. 500-540.
Shapiro, 2017, Bone Marrow aspiration for regenerative orthopedic intervention: technique with ultrasound guidance for needle placement, Regenerative Medicine, 12:8, 917-928.
Trepanning, from Wikipedia, the free encyclopedia pp. 1-7, downloaded Sep. 27, 2022.
Yousefi, 2018, Producing Covalent Microarrays of Amine-Conjugated DNA Probes on Various Functional Surfaces to Create Stable and Reliable Biosensors, Advanced Materials Interfaces, 5(16):1800659.
Yu, 2016, G-CSF and hypoxic conditioning improve the proliferation, neural differentiation and migration of canine bone marrow mesenchymal stem cells, Experimental and Therapeutic Medicine, 12:1822-1828.
Zeng, 2002, Unique patterns of surface receptors, cytokine secretion, and immune functions distinguish T cells in the bone marrow from those in the periphery: impact on allogenic bone marrow transplantation, Blood, 99 (4):1449-1457.
Zuber, 2017, Mechanisms of Mixed Chimerism-Based Transplant Tolerance, Trends In Immunology, 38(11):829-843.

COMPOSITIONS FOR ESTABLISHING MIXED CHIMERISM AND METHODS OF MANUFACTURE THEREOF

CROSS-REFERENCE TO RELATED APPLICATION

This application claims the benefit of, and priority to, U.S. Non-provisional Patent Application No. 15/946,099, filed Apr. 5, 2018, the contents of which are incorporated by reference.

FIELD OF THE INVENTION

The invention relates to compositions for establishing mixed chimerism in a subject and methods of manufacture and use thereof.

BACKGROUND

Over 30,000 people receive organ transplants annually in the United States. Although an organ transplant can save or transform the recipient's life, transplantation remains a risky procedure. A major concern is that the recipient's immune system will identify the transplanted organ as foreign and destroy it. For example, the rate of rejection for kidney transplants, the most common type of solid organ transplant, is about 25%. Consequently, most transplant recipients must take immunosuppressive drugs for the rest of their lives. Immunosuppressive therapy, however, carries its own set of risks, including increased risk of infection, cancer, hypertension, and liver damage.

To date, the only way to maintain long-term graft tolerance in humans without immunosuppression is to reconstruct the recipient's immune system to include a mixture of donor-derived and recipient-derived hematopoietic cells. Mixed chimerism is established by providing hematopoietic cellular compositions that include $CD34^+$ and $CD3^+$ cells (See Strober et al., U.S. Pat. Nos. 9,504,717 and 9,561,253). The manufacture of such hematopoietic cellular compositions starts by obtaining an apheresis product from an organ donor. The apheresis product includes $CD34^+$ and $CD3^+$ cells. After certain initial work-up steps, the apheresis product is purified to enrich for the $CD34^+$ cells in the apheresis product. To enrich for the $CD34^+$ cells, the entire apheresis product is flowed through an immunomagnetic-bead column, e.g., an Isolex column. The $CD34^+$ cells are retained by the immunomagnetic-bead column. The column flow through of the apheresis product (column effluent) is collected and includes the $CD3^+$ cells, which are not retained by the immunomagnetic-bead column. The enriched $CD34^+$ cells are then eluted from the immunomagnetic-bead column. A defined amount of the column effluent having the $CD3^+$ cells is then added to the enriched $CD34^+$ cells until a desired concentration of $CD3^+$ cells is achieved.

SUMMARY

The invention recognizes that there is a need for a more commercially amenable high throughput manufacturing process for making hematopoietic cellular compositions. The invention provides new methods for manufacturing hematopoietic cellular compositions and new hematopoietic cellular compositions for establishing mixed chimerism. Particularly, the invention provides an approach in which an entire apheresis product is not flowed through a $CD34^+$ cell enriching column. Rather than flowing the entire apheresis product through a $CD34^+$ cell enriching column, the apheresis product, which includes $CD34^+$ and $CD3^+$ cells, is divided into a first portion and a second portion. The first portion of the apheresis product is purified, e.g., by flow through the $CD34^+$ cell enriching column, to obtain an enriched amount of $CD34^+$ cells. The second portion of the apheresis product is not flowed through the $CD34^+$ cell enriching column. To complete the manufacture of the hematopoietic cellular compositions of the invention, at least some of the second portion of the apheresis product, comprising $CD34^+$ and $CD3^+$ cells, is introduced to the enriched amount of $CD34^+$ cells. In this approach, the $CD3^+$ cells that make-up the hematopoietic cellular compositions of the invention are not flowed through a $CD34^+$ cell enriching column and in fact never interact with the $CD34^+$ cell enriching column. Importantly, the column effluent does not need to be retained for the hematopoietic cellular compositions of the invention. By obviating the need to retain the column effluent, the methods can more easily be modified for large-scale product preparation. In that manner, the invention provides commercial manufacturing methods that are robust, efficient, scalable, and reproducible, while also providing hematopoietic cellular compositions in which the $CD3^+$ cells that make-up the hematopoietic cellular compositions of the invention are not flowed through a $CD34^+$ cell enriching column.

In certain aspects, the invention provides cellular products for establishing mixed chimerism in a solid organ transplant recipient. The cellular products include column-purified $CD34^+$ cells derived from an apheresis product and $CD3^+$ cells derived from the apheresis product that have not passed through a purification column. In other aspects, the invention provides cellular products including column purified $CD34^+$ cells derived from an apheresis product, and $CD3^+$ cells derived from the apheresis product that have not passed through a purification column. In other aspects, the invention provides cellular products including component A and component B, in which component A includes $CD34^+$ cells that have been purified from a first portion of a non-column purified apheresis product, and in which component B includes a second portion of the non-column purified apheresis product including $CD3^+$. Unlike prior hematopoietic cellular compositions that included purified $CD34^+$ cells combined with column effluent including $CD3^+$ cells, the hematopoietic cellular compositions of the invention do not include column effluent.

In another aspect, the invention provides methods for manufacturing a cellular product for establishing mixed chimerism in a solid organ transplant recipient. The methods include receiving an apheresis product containing $CD34^+$ and $CD3^+$ cells; dividing the apheresis product into a first portion and a second portion; purifying the first portion to obtain an enriched amount of $CD34^+$ cells; and introducing at least some of the second portion containing $CD3^+$ cells to the enriched amount of $CD34^+$ cells.

The compositions of the invention can include various concentrations for each of the $CD34^+$ cells and $CD3^+$ cells, and different concentrations are discussed herein. The amount may be specified as a number of cells relative to the body mass of the recipient. For example, the cellular product may contain at least $1 \times 10^5$, $2 \times 10^5$, $5 \times 10^5$, $1 \times 10^6$, $2 \times 10^6$, or $4 \times 10^6$ $CD34^+$ cells/kg recipient weight. The cellular product may contain at least $1 \times 10^4$, $2 \times 10^4$, $5 \times 10^4$, $1 \times 10^5$, $2 \times 10^5$, $5 \times 10^5$, $1 \times 10^6$, $2 \times 10^6$, $5 \times 10^6$, $1 \times 10^7$, $2 \times 10^7$, $5 \times 10^7$, or $1 \times 10^8$ $CD3^+$ cells/kg recipient weight.

The $CD34^+$ cells and $CD3^+$ cells may be provided in separate containers. The $CD34^+$ cells and $CD3^+$ cells may be provided as a mixture in the same container. The cellular product may be cryopreserved. The cellular product may contain one or more cryoprotectants. The cryoprotectant may be dextran having an average molecular weight of 40,000 Da or DMSO. The cellular product may contain the cryoprotectant at a concentration of about 1%, 2%, 3%, 4%, 5%, 7.5%, or 10%.

The $CD34^+$ cells, the $CD3^+$ cells, or both may be derived from the solid organ transplant donor. The donor and the recipient may be HLA-matched, or they may be HLA-mismatched. The donor and recipient may be HLA-matched at six, eight, ten, or twelve alleles among the HLA-A, HLA-B, HLA-C, HLA-DP, HLA-DQ, and HLA-DR genes. The donor and recipient may be HLA-mismatched at one, two, three, four, five, six, or more alleles among the HLA-A, HLA-B, HLA-C, HLA-DP, HLA-DQ, and HLA-DR genes.

The $CD34^+$ cells may be column-purified by any acceptable cell purification method. For example, the $CD34^+$ cells may be immunopurified using immunomagnetic particles and a magnetic column.

The $CD34^+$ cells and $CD3^+$ cells may be obtained from a single apheresis product. The $CD34^+$ cells and $CD3^+$ cells may be obtained from multiple apheresis products, for example, two, three, four, five, six, or more apheresis products. The $CD34^+$ cells and $CD3^+$ cells may be obtained from a cryopreserved apheresis product. The $CD34^+$ cells may be column-purified prior to cryopreservation or after cryopreservation.

DETAILED DESCRIPTION

The primary hurdle in organ transplantation is getting the recipient to tolerate the donor's tissue. If the recipient's immune system detects the donated organ as foreign, it attacks the tissue, leading to graft rejection. Consequently, most transplant recipients must take drugs that suppress the immune system. Immunosuppressive therapy, however, creates its own set of risks. For example, immunosuppressive drugs decrease the body's ability to ward off infections. In addition, because they hinder the immune system's ability to identify and destroy malignant tissue, immunosuppressive drugs increase the risk of developing cancer.

To avoid graft rejection, transplantation of solid organs may be accompanied by transfer of donor-derived blood cell progenitors. Providing donor blood cells allows reconstitution of the recipient's immune system to include cells that have been educated to recognize the organ as non-foreign tissue. Consequently, the donated organ is not attacked, and the recipient tolerates the graft.

One strategy for reconstructing the recipient's immune system entails complete replacement of the recipient's hematopoietic system with exclusively donor-derived cells to achieve a state of full chimerism. A risk associated with full chimerism, however, is that the completely donor-derived immune system may identify the recipient's tissue as foreign and attack it, a condition called graft-versus-host disease (GVHD). See, e.g., Sach et al., Induction of Tolerance through Mixed Chimerism, Cold Spring Harb Perspect Med 2014; 4:a015529, doi: 10.1101/cshperspect.a015529, the contents of which are incorporated herein by reference. As a result, fully chimeric patients must remain on immunosuppressive therapy indefinitely.

Another strategy is to repopulate the recipient's immune system with a mixture of donor-derived cells and recipient-derived cells to attain a state called mixed chimerism. Compared to full chimerism, mixed chimerism is associated with lower rates of GVHD. In addition, mixed chimeric regimens require lower doses of immunosuppressive therapy initially and allow complete discontinuation of immunosuppression after the stability of the recipient's mixed chimerism has been established. To date, induction of mixed chimerism is the only method of producing graft tolerance in humans without maintaining immunosuppressive therapy.

The compositions of the invention are useful for establishing mixed chimerism in a solid organ transplant recipient. It is recognized in the art that providing donor-derived $CD34^+$ cells and $CD3^+$ cells in conjunction with solid organ transplants facilitates the maintenance of mixed chimerism. The present invention provides improved compositions for establishing mixed chimerism in solid organ transplant recipients and methods of making and using such compositions.

Cellular Products

All blood cells, including the cells of the immune system, are derived from hematopoietic stem cells (HSCs). HSCs are multipotent cells that can differentiate into various specialized cells and also reproduce to generate new HSCs. HSCs that differentiate form either lymphoid progenitors or myeloid progenitors. Lymphoid progenitors give rise to lymphocytes and natural killer cells. Myeloid progenitors produce cells of the myeloid and erythroid lineages, such as erythrocytes, platelets, basophils, neutrophils, eosinophils, monocytes, macrophages, and antigen-presenting cells, such as dendritic cells. In adults, most hematopoietic development occurs in the bone marrow, although maturation and activation of some lymphoid cells occurs in the spleen, thymus, and lymph nodes.

The cellular products of the invention include two populations of cells that allow donor HSCs to develop into mature cells of the immune system in the recipient's body. One population includes $CD34^+$ cells. CD34 is a cell surface marker that is expressed in HSCs and their immediate descendants, multipotent progenitor cells, which have not committed to either the myeloid or lymphoid lineage. Consequently, CD34 expression is a useful measure for identifying populations of cells that contain HSCs. The other population includes $CD3^+$ cells. CD3 comprises a group of polypeptides that interact with the two polypeptide chains of the T cell receptor to form the T cell receptor complex. The CD3 complex includes a gamma chain, delta chain, and two epsilon chains. CD3 is expressed on the surface of mature T cells and is thus useful as a marker for T cells.

To promote establishment of mixed chimerism in the recipient, the cellular products include $CD34^+$ cells and $CD3^+$ cells in appropriate quantities. For example, an ample supply of $CD34^+$ cells is necessary to develop a stable population of donor-derived immune cells in the recipient. However, $CD34^+$ cells are relatively scarce, making up only about 0.1-0.2% of peripheral blood cells in normal, untreated patients. Therefore, the cellular products contain $CD34^+$ cells that have been column purified from an apheresis product to obtain a sufficient number of such cells. In contrast, $CD3^+$ cells are abundant, accounting for a majority of mononuclear cells in the peripheral blood. Thus, the population of $CD3^+$ cells in the cellular products is taken from a portion of the apheresis product that has not been subjected to a column purification step. Avoiding unnecessary manipulation of the $CD3^+$ population used in the cellular products has several advantages. First, it minimizes the opportunity for cells to become damaged and therefore preserves cell viability. In addition, it allows the $CD3^+$ fraction to retain circulating factors from the donor's blood that may facilitate hematopoiesis in the recipient. Finally, it simplifies the preparation of the cellular products.

The cellular products may contain CD34+ cells and CD3+ cells in defined amounts. A useful unit of cell quantity in a product is the number of cells relative to the body mass of the recipient. For example and without limitation, the cellular product may contain at least $1\times10^4$, $2\times10^4$, $5\times10^4$, $1\times10^5$, $2\times10^5$, $5\times10^5$, $1\times10^6$, $2\times10^6$, or $4\times10^6$, $1\times10^7$, $2\times10^7$, $4\times10^7$, or $1\times10^8$ CD34+ cells/kg recipient weight. For example and without limitation, the cellular product may contain at least $1\times10^4$, $2\times10^4$, $5\times10^4$, $1\times10^5$, $2\times10^5$, $5\times10^5$, $1\times10^6$, $2\times10^6$, $5\times10^6$, $1\times10^7$, $2\times10^7$, $5\times10^7$, or $1\times10^8$ CD3+ cells/kg recipient weight. Other concentrations are exemplified in each of Strober et al., U.S. Pat. No. 9,504,717 and Strober et al., U.S. Pat. No. 9,561,253, the content of each of which is incorporated by reference herein in its entirety.

The cellular product may contain CD34+ cells at a designated level of purity. For example, the cellular product may contain CD34+ cells that are at least 30%, at least 40%, at least 50%, at least 60%, at least 70%, at least 80%, at least 90%, at least 95%, at least 98%, or at least 99% pure. Other purities are exemplified in each of Strober et al., U.S. Pat. No. 9,504,717 and Strober et al., U.S. Pat. No. 9,561,253, the content of each of which is incorporated by reference herein in its entirety.

The CD34+ cells and CD3+ cells may be derived from any donor. The CD34+ cells and CD3+ cells may be from the same donor. The CD34+ cells and CD3+ cells may be from different donors. Preferably, the CD34+ cells and CD3+ cells are derived from the donor of the solid organ that is being or has been transplanted into the recipient. The CD34+ cells and CD3+ cells may be derived from a living donor. The CD34+ cells and CD3+ cells may be derived from a deceased donor.

The CD34+ cells and CD3+ cells may be provided as a mixture in one or more containers. The CD34+ cells and CD3+ cells may be provided in separate container. Any commercially available container approved to hold cellar products may be used.

The cellular product may be provided frozen. Consequently, the cellular product may contain a cryoprotectant. Any cryoprotectant known in the art may be used. For example and without limitation, the cryoprotectant may be DMSO, dextran having an average molecular weight of 40 kDa, serum, e.g., bovine serum, albumin, e.g., human serum albumin, or cell culture medium. The cryoprotectant may be present at a defined concentration. For example, the cellular product may contain about 1% DMSO, about 2% DMSO, about 5% DMSO, about 7.5% DMSO, about 10% DMSO, about 12.5% DMSO, about 15% DMSO, or about 20% DMSO. The cellular product may contain about 1% dextran, about 2% dextran, about 5% dextran, about 7.5% dextran, about 10% dextran, about 12.5% dextran, about 15% dextran, or about 20% dextran. Cyroprotection is discussed in each of Strober et al., U.S. Pat. No. 9,504,717 and Strober et al., U.S. Pat. No. 9,561,253, the content of each of which is incorporated by reference herein in its entirety.

The cellular product may contain agents that enhance engraftment or functional mobilization of the hematopoietic cells in the recipient. The cellular product may contain agents that prevent a negative reaction of the recipient to the hematopoietic cells. For example and without limitation, the pharmaceutical composition may contain a cytokine, chemokine, growth factor, excipient, carrier, antibody or a fragment thereof, small molecule, drug, agonist, antagonist, matrix protein, or complementary cell type.

The cellular product may contain a buffer. The cellular product may be buffer to maintain physiologically compatible pH. For example, the cellular product may be buffered to a neutral pH, such as from about 6.0 to about 8.0.

The cellular product can be supplied in the form of a pharmaceutical composition, comprising an isotonic excipient prepared under sufficiently sterile conditions for human administration. Choice of the cellular excipient and any accompanying elements of the composition is adapted in accordance with the route and device used for administration. For general principles in medicinal formulation, see Cell Therapy: Stem Cell Transplantation, Gene Therapy, and Cellular Immunotherapy, by G. Morstyn & W. Sheridan. eds., Cambridge University Press, 1996; and Hematopoietic Stem Cell Therapy, E. D. Ball, J. Lister & P. Law, Churchill Livingstone, 2000.

The donor cells may be HLA-matched or HLA-mismatched to the recipient. Human leukocyte antigens (HLAs), also called major histocompatibility complex (MHC) antigens, are protein molecules expressed on the surface of cells that confer a unique antigenic identity to these cells. MHC/HLA antigens are target molecules that are recognized by T-cells and natural killer (NK) cells as being derived from the same source of hematopoietic stem cells as the immune effector cells ("self") or as being derived from another source of hematopoietic reconstituting cells ("non-self"). Two main classes of HLA antigens are recognized: HLA class I and HLA class II. HLA class I antigens (A, B, and C in humans) render each cell recognizable as "self," whereas HLA class II antigens (DR, DP, and DQ in humans) are involved in reactions between lymphocytes and antigen presenting cells.

A key aspect of the HLA gene system is its polymorphism. Each gene exists in different alleles. Allelic gene products differ in one or more amino acids in the alpha and/or beta domain(s). An individual has two alleles of each gene, for a total of twelve alleles among the HLA-A, HLA-B, HLA-C, HLA-DP, HLA-DQ, and HLA-DR genes. An HLA-matched donor may have a match with the recipient at six, eight, ten, or twelve alleles selected from any combination of the HLA-A, HLA-B, HLA-C, HLA-DP, HLA-DQ, and HLA-DR genes. The genes most important for HLA typing are HLA-A, HLA-B, and HLA-DR, so the donor and recipient may be matched at all six alleles of the HLA-A, HLA-B, and HLA-DR genes. An HLA-mismatched donor may have a mismatch at one, two, three, four, five, six, or more alleles among the HLA-A, HLA-B, HLA-C, HLA-DP, HLA-DQ, and HLA-DR genes. HLA typing may be performed by any method known in the art. Examples of HLA typing methods include serological cytotoxicity, flow cytometry, and DNA typing. Such methods are described in, for example, U.S. Pat. No. 9,561,253, the contents of which are incorporated herein by reference.

The HLA genes are clustered in a super-locus present on chromosome position 6p21. Consequently, the set of alleles present on a single chromosome, i.e., a haplotype, tends to be inherited as a group. Identifying a patient's haplotypes can help predict the probability of finding matching donors and assist in developing a search strategy. Haplotypes vary in how common they are among the general population and in their frequency within different racial and ethnic groups.

Numerous exemplary embodiments are now described below, both HLA matched and HLA mismatched. The skilled artisan will recognize that the below embodiments are exemplary and non-limiting, particularly, the below embodiments do not limit any other part or exemplified cell amounts or combinations in any other part of this application.

The cellular product may contain column-purified CD34$^+$ cells derived from an apheresis product in an amount of at least $5\times10^5$ CD34$^+$ cells/kg recipient weight and CD3$^+$ cells derived from the apheresis product that have not passed through a purification column in an amount of at least $1\times10^5$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $5\times10^5$ CD34$^+$ cells/kg recipient weight and CD3$^+$ cells derived from the apheresis product that have not passed through a purification column in an amount of at least $2\times10^5$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $5\times10^5$ CD34$^+$ cells/kg recipient weight and CD3$^+$ cells derived from the apheresis product that have not passed through a purification column in an amount of at least $5\times10^5$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $5\times10^5$ CD34$^+$ cells/kg recipient weight and CD3$^+$ cells derived from the apheresis product that have not passed through a purification column in an amount of at least $1\times10^6$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $4\times10^6$ CD34$^+$ cells/kg recipient weight and CD3$^+$ cells derived from the apheresis product that have not passed through a purification column in an amount of at least $1\times10^6$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $4\times10^6$ CD34$^+$ cells/kg recipient weight and CD3$^+$ cells derived from the apheresis product that have not passed through a purification column in an amount of $1\times10^6$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $5\times10^5$ CD34$^+$ cells/kg recipient weight and CD3$^+$ cells derived from the apheresis product that have not passed through a purification column in an amount of at least $2\times10^6$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $5\times10^5$ CD34$^+$ cells/kg recipient weight and CD3$^+$ cells derived from the apheresis product that have not passed through a purification column in an amount of at least $1\times10^7$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $5\times10^5$ CD34$^+$ cells/kg recipient weight and CD3$^+$ cells derived from the apheresis product that have not passed through a purification column in an amount of at least $1\times10^8$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $5\times10^5$ CD34$^+$ cells/kg recipient weight and CD3$^+$ cells derived from the apheresis product that have not passed through a purification column in an amount of at least $1\times10^9$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $5\times10^5$ CD34$^+$ cells/kg recipient weight and CD3$^+$ cells derived from the apheresis product that have not passed through a purification column in an amount of at least $5\times10^6$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $5\times10^5$ CD34$^+$ cells/kg recipient weight and CD3$^+$ cells derived from the apheresis product that have not passed through a purification column in an amount of at least $1\times10^7$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $5\times10^5$ CD34$^+$ cells/kg recipient weight and CD3$^+$ cells derived from the apheresis product that have not passed through a purification column in an amount of at least $2\times10^7$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $5\times10^5$ CD34$^+$ cells/kg recipient weight and CD3$^+$ cells derived from the apheresis product that have not passed through a purification column in an amount of at least $5\times10^7$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $5\times10^5$ CD34$^+$ cells/kg recipient weight and CD3$^+$ cells derived from the apheresis product that have not passed through a purification column in an amount of at least $1\times10^8$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $1\times10^6$ CD34$^+$ cells/kg recipient weight and CD3$^+$ cells derived from the apheresis product that have not passed through a purification column in an amount of at least $1\times10^5$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $1\times10^6$ CD34$^+$ cells/kg recipient weight and CD3$^+$ cells derived from the apheresis product that have not passed through a purification column in an amount of at least $2\times10^5$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $1\times10^6$ CD34$^+$ cells/kg recipient weight and CD3$^+$ cells derived from the apheresis product that have not passed through a purification column in an amount of at least $5\times10^5$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $1\times10^6$ CD34$^+$ cells/kg recipient weight and CD3$^+$ cells derived from the apheresis product that have not passed through a purification column in an amount of at least $1\times10^6$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $1\times10^6$ CD34$^+$ cells/kg recipient weight and CD3$^+$ cells derived from the apheresis product that have not passed through a purification column in an amount of at least $2\times10^6$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $1\times10^6$ CD34$^+$ cells/kg recipient weight and CD3$^+$ cells derived from the apheresis product that have not passed through a purification column in an amount of at least $5\times10^6$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $1\times10^6$ CD34$^+$ cells/kg recipient weight and CD3$^+$ cells derived from the apheresis product that have not passed through a purification column in an amount of at least $1\times10^7$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $1\times10^6$ CD34$^+$ cells/kg recipient weight and CD3$^+$ cells derived from the apheresis product that have not passed through a purification column in an amount of at least $2\times10^7$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $1\times10^6$ CD34$^+$ cells/kg recipient weight and CD3$^+$ cells derived from the apheresis product that have not passed through a purification column in an amount of at least $5\times10^7$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $1\times10^6$ CD34$^+$ cells/kg recipient weight and CD3$^+$ cells derived from the apheresis product that have not passed through a purification column in an amount of at least $1\times10^8$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $2\times10^6$ CD34$^+$ cells/kg recipient weight and CD3$^+$ cells derived from the apheresis product that have not passed through a purification column in an amount of at least $1\times10^5$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $2\times10^6$ CD34$^+$ cells/kg recipient weight and CD3$^+$ cells derived from the apheresis product that have not passed through a purification column in an amount of at least $2\times10^5$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $2\times10^6$ CD34$^+$ cells/kg recipient weight and CD3$^+$ cells derived from the apheresis product that have not passed through a purification column in an amount of at least $5\times10^5$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $2\times10^6$ CD34$^+$ cells/kg recipient weight and CD3$^+$ cells derived from the apheresis product that have not passed through a purification column in an amount of at least $1\times10^6$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $2\times10^6$ CD34$^+$ cells/kg recipient weight and CD3$^+$ cells derived from the apheresis product that have not passed through a purification column in an amount of at least $2\times10^6$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $2\times10^6$ CD34$^+$ cells/kg recipient weight and CD3$^+$ cells derived from the apheresis product that have not passed through a purification column in an amount of at least $5\times10^6$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $2\times10^6$ CD34$^+$ cells/kg recipient weight and CD3$^+$ cells derived from the apheresis product that have not passed through a purification column in an amount of at least $1\times10^7$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $2\times10^6$ CD34$^+$ cells/kg recipient weight and CD3$^+$ cells derived from the apheresis product that have not passed through a purification column in an amount of at least $2\times10^7$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $2\times10^6$ CD34$^+$ cells/kg recipient weight and CD3$^+$ cells derived from the apheresis product that have not passed through a purification column in an amount of at least $5\times10^7$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $2\times10^6$ CD34$^+$ cells/kg recipient weight and CD3$^+$ cells derived from the apheresis product that have not passed through a purification column in an amount of at least $1\times10^8$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $4\times10^6$ CD34$^+$ cells/kg recipient weight and CD3$^+$ cells derived from the apheresis product that have not passed through a purification column in an amount of at least $1\times10^5$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $4\times10^6$ CD34$^+$ cells/kg recipient weight and CD3$^+$ cells derived from the apheresis product that have not passed through a purification column in an amount of at least $2\times10^5$ CD3$^+$ cells/kg recipient weight, the CD34$^+$ cells and CD3$^+$ cells being HLA-matched to the recipient.

The cellular product may contain column-purified CD34$^+$ cells derived from an apheresis product in an amount of at least $4\times10^6$ CD34$^+$ cells/kg recipient weight and CD3$^+$ cells derived from the apheresis product that have not passed through a purification column in an amount of at least $5\times10^5$ $CD3^+$ cells/kg recipient weight, the $CD34^+$ cells and $CD3^+$ cells being HLA-matched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $1\times10^6$ $CD3^+$ cells/kg recipient weight, the $CD34^+$ cells and $CD3^+$ cells being HLA-matched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $2\times10^6$ $CD3^+$ cells/kg recipient weight, the $CD34^+$ cells and $CD3^+$ cells being HLA-matched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $5\times10^6$ $CD3^+$ cells/kg recipient weight, the $CD34^+$ cells and $CD3^+$ cells being HLA-matched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $1\times10^7$ $CD3^+$ cells/kg recipient weight, the $CD34^+$ cells and $CD3^+$ cells being HLA-matched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $2\times10^7$ $CD3^+$ cells/kg recipient weight, the $CD34^+$ cells and $CD3^+$ cells being HLA-matched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $5\times10^7$ $CD3^+$ cells/kg recipient weight, the $CD34^+$ cells and $CD3^+$ cells being HLA-matched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $1\times10^8$ $CD3^+$ cells/kg recipient weight, the $CD34^+$ cells and $CD3^+$ cells being HLA-matched to the recipient.

The cellular product may contain column-purified $CD34^+$ cells derived from an apheresis product in an amount of at least $5\times10^5$ $CD34^+$ cells/kg recipient weight and $CD3^+$ cells derived from the apheresis product that have not passed through a purification column in an amount of at least $1\times10^5$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $5\times10^5$ $CD34^+$ cells/kg recipient weight and $CD3^+$ cells derived from the apheresis product that have not passed through a purification column in an amount of at least $2\times10^5$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $5\times10^5$ $CD34^+$ cells/kg recipient weight and $CD3^+$ cells derived from the apheresis product that have not passed through a purification column in an amount of at least $5\times10^5$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $5\times10^5$ $CD34^+$ cells/kg recipient weight and $CD3^+$ cells derived from the apheresis product that have not passed through a purification column in an amount of at least $1\times10^6$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $5\times10^5$ $CD34^+$ cells/kg recipient weight and $CD3^+$ cells derived from the apheresis product that have not passed through a purification column in an amount of at least $2\times10^6$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $5\times10^5$ $CD34^+$ cells/kg recipient weight and $CD3^+$ cells derived from the apheresis product that have not passed through a purification column in an amount of at least $5\times10^6$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $5\times10^5$ $CD34^+$ cells/kg recipient weight and $CD3^+$ cells derived from the apheresis product that have not passed through a purification column in an amount of at least $1\times10^7$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $5\times10^5$ $CD34^+$ cells/kg recipient weight and $CD3^+$ cells derived from the apheresis product that have not passed through a purification column in an amount of at least $2\times10^7$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $5\times10^5$ $CD34^+$ cells/kg recipient weight and $CD3^+$ cells derived from the apheresis product that have not passed through a purification column in an amount of at least $5\times10^7$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $5\times10^5$ $CD34^+$ cells/kg recipient weight and $CD3^+$ cells derived from the apheresis product that have not passed through a purification column in an amount of at least $1\times10^8$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $1\times10^6$ $CD34^+$ cells/kg recipient weight and $CD3^+$ cells derived from the apheresis product that have not passed through a purification column in an amount of at least $1\times10^5$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $1\times10^6$ $CD34^+$ cells/kg recipient weight and $CD3^+$ cells derived from the apheresis product that have not passed through a purification column in an amount of at least $2\times10^5$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $1\times10^6$ $CD34^+$ cells/kg recipient weight and $CD3^+$ cells derived from the apheresis product that have not passed through a purification column in an amount of at least $5\times10^5$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $1\times10^6$ $CD34^+$ cells/kg recipient weight and $CD3^+$ cells derived from the apheresis product that have not passed through a purification column in an amount of at least $1\times10^6$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $1\times10^6$ $CD34^+$ cells/kg recipient weight and $CD3^+$ cells derived from the apheresis product that have not passed through a purification column in an amount of at least $2\times10^6$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $1\times10^6$ $CD34^+$ cells/kg recipient weight and $CD3^+$ cells derived from the apheresis product that have not passed through a purification column in an amount of at least $5\times10^6$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $1\times10^6$ $CD34^+$ cells/kg recipient weight and $CD3^+$ cells derived from the apheresis product that have not passed through a purification column in an amount of at least $1\times10^7$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $1\times10^6$ $CD34^+$ cells/kg recipient weight and $CD3^+$ cells derived from the apheresis product that have not passed through a purification column in an amount of at least $2\times10^7$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $1\times10^6$ $CD34^+$ cells/kg recipient weight and $CD3^+$ cells derived from the apheresis product that have not passed through a purification column in an amount of at least $5\times10^7$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $1\times10^6$ $CD34^+$ cells/kg recipient weight and $CD3^+$ cells derived from the apheresis product that have not passed through a purification column in an amount of at least $1\times10^8$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $2\times10^6$ $CD34^+$ cells/kg recipient weight and $CD3^+$ cells derived from the apheresis product that have not passed through a purification column in an amount of at least $1\times10^5$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $2\times10^6$ $CD34^+$ cells/kg recipient weight and $CD3^+$ cells derived from the apheresis product that have not passed through a purification column in an amount of at least $2\times10^5$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $2\times10^6$ $CD34^+$ cells/kg recipient weight and $CD3^+$ cells derived from the apheresis product that have not passed through a purification column in an amount of at least $5\times10^5$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $2\times10^6$ $CD34^+$ cells/kg recipient weight and $CD3^+$ cells derived from the apheresis product that have not passed through a purification column in an amount of at least $1\times10^6$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $2\times10^6$ $CD34^+$ cells/kg recipient weight and $CD3^+$ cells derived from the apheresis product that have not passed through a purification column in an amount of at least $2\times10^6$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $2\times10^6$ $CD34^+$ cells/kg recipient weight and $CD3^+$ cells derived from the apheresis product that have not passed through a purification column in an amount of at least $5\times10^6$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $2\times10^6$ $CD34^+$ cells/kg recipient weight and $CD3^+$ cells derived from the apheresis product that have not passed through a purification column in an amount of at least $1\times10^7$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $2\times10^6$ $CD34^+$ cells/kg recipient weight and $CD3^+$ cells derived from the apheresis product that have not passed through a purification column in an amount of at least $2\times10^7$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $2\times10^6$ $CD34^+$ cells/kg recipient weight and $CD3^+$ cells derived from the apheresis product that have not passed through a purification column in an amount of at least $5\times10^7$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $2\times10^6$ $CD34^+$ cells/kg recipient weight and $CD3^+$ cells derived from the apheresis product that have not passed through a purification column in an amount of at least $1\times10^8$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $1\times10^5$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $2\times10^5$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $5\times10^5$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $1\times10^6$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $2\times10^6$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $5\times10^6$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $1\times10^7$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $2\times10^7$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $5\times10^7$ $CD3^+$ cells/kg recipient weight, the $CD34^+$ cells and $CD3^+$ cells being HLA-mismatched to the recipient.

The cellular product may contain column-purified $CD34^+$ cells derived from an apheresis product in an amount of at least $4\times10^6$ $CD34^+$ cells/kg recipient weight and $CD3^+$ cells derived from the apheresis product that have not passed through a purification column in an amount of at least $1\times10^8$ $CD3^+$ cells/kg recipient weight, the $CD34^+$ cells and $CD3^+$ cells being HLA-mismatched to the recipient.

Preparation of Cellular Products

The cellular products of the invention are prepared from one or more apheresis products. Preferably, the one or more apheresis products are divided into two portions: one portion for column-purification of $CD34^+$ cells, and one portion to serve as the source of $CD3^+$ cells. When multiple apheresis products are used, they may be combined and then divided into portions. Alternatively, individual apheresis products can be divided into portions, and the portions from individual apheresis products can be combined. Preferably, the apheresis products are obtained from the solid organ donor. Apheresis methods are known in the art and described in, for example, U.S. Pat. No. 9,561,253, the contents of which are incorporated herein by reference.

As indicated above, $CD34^+$ cells make up a low percentage of peripheral blood cells in normal subjects. However, the fraction of $CD34^+$ cells in blood can be increased by administering to the subject a factor, such as granulocyte colony stimulating factor (G-CSF), that mobilizes $CD34^+$ cells from bone marrow and other sources. Thus, prior to apheresis, the subject may be given G-CSF to mobilize $CD34^+$ cells. Regimens for administering G-CSF to a subject prior to apheresis, including the dosage, frequency, and timing of administration, are known in the art and described in, for example, U.S. Pat. No. 9,561,253, the contents of which are incorporated herein by reference.

During preparation of the cellular products of the invention, cells may be frozen at any stage. For example, cells may be frozen immediately after an apheresis product is isolated from a donor but prior to separation into fractions, after separation into fractions, after column-purification or enrichment of $CD34^+$ cells, or after combining column-purified $CD34^+$ cells with $CD3^+$ cells.

Cryopreservation of compositions of the invention may include addition of a cryoprotectant, such as a cryoprotectant described above. Cryopreservation typically involves reducing the temperature of the cell-containing sample at a controlled rate. Cryopreservation may include thawing the cell-containing sample and washing the sample to remove one or more cryoprotectants. Methods and reagents for cryopreservation, including freezing, thawing, and washing samples, are known in the art and described in, for example, U.S. Pat. No. 9,561,253, the contents of which are incorporated herein by reference.

$CD34^+$ cells may be column-purified based on qualitative or quantitative expression of one or more cell surface markers. Examples of suitable cell surface markers include CD34, Thy-1, CD38, and AC133. $CD34^+$ cells may be column-purified based on the presence or absence of a marker or on the level of expression of a marker, e.g., high vs. low.

$CD34^+$ cells may be column-purified by selectively binding a suitable affinity reagent to CD34 or another marker. The affinity reagent may be an antibody, a full-length antibody, a fragment of an antibody, a naturally occurring antibody, a synthetic antibody, an engineered antibody, a full-length affibody, a fragment of an affibody, a full-length affilin, a fragment of an affilin, a full-length anticalin, a fragment of an anticalin, a full-length avimer, a fragment of an avimer, a full-length DARPin, a fragment of a DARPin, a full-length fynomer, a fragment of a fynomer, a full-length kunitz domain peptide, a fragment of a kunitz domain peptide, a full-length monobody, a fragment of a monobody, a peptide, a polyaminoacid, or the like. The affinity reagent may be directly conjugated to a detection reagent and/or purification reagent. The detection reagent and purification reagent may be the same, or they may be different. For example, the detection reagent and/or purification reagent may be fluorescent, magnetic, or the like. The detection reagent and/or purification reagent may be a magnetic particle for column purification, e.g., an immunomagnetic microsphere.

$CD34^+$ cells may be column-purified from other cells using any suitable method. For example, $CD34^+$ cells may be column-purified using an immunomagnetic column system, such as those sold under the trade name CliniMACS by Miltenyi Biotec Inc. (Auburn, Calif.), Methods of affinity purification of hematopoietic cells, including $CD34^+$ cells, and analysis of purified populations are described in, for example, U.S. Pat. Nos. 9,561,253; 9,452,184; Ng et al., Isolation of human and mouse hematopoietic stem cells, Methods Mol Biol. (2009) 506:13-21. doi: 10.1007/978-1-59745-409-4_2; and Spohn et al., Automated $CD34^+$ cell isolation of peripheral blood stem cell apheresis product, Cytotherapy (2015) October; 17(10):1465-71. doi: 10.1016/j.jcyt.2015.04.005, the contents of each of which are incorporated herein by reference. The methods may include positive selection, negative selection, or both.

$CD34^+$ cells may be isolated, enriched, or purified by other methods in addition to column-purification. For example, $CD34^+$ cells may be isolated, enriched, or purified by flow cytometry, cell sorting, or immunoadsorption column separation.

$CD34^+$ cells and/or $CD3^+$ cells may be expanded ex vivo. Expansion may occur prior to, or subsequent to, freezing. Expansion may include providing one or more growth factors, and it may include culturing cells in the presence of another cell type, e.g., feeder cells. Methods for expanding hematopoietic cells are described in, for example, U.S. Pat. No. 9,561,253, the contents of which are incorporated herein by reference.

Providing Cellular Products

The cellular products of the invention may be provided to the recipient of a solid organ transplant. The cellular product may be provided by any suitable means. For example and without limitation, the $CD34^+$ cells and/or $CD3^+$ cells may be delivered to the recipient by injection using a needle, catheter, central line or the like. In some cases, the cells may be delivered intravascularly, intravenously, intraarterially, subcutaneously, intramuscularly, directly to the bone, or through any source which permits the hematopoietic cells to home to an appropriate site in the recipient such that the hematopoietic cells persist, regenerate and differentiate in the recipient. The $CD34^+$ cells and/or $CD3^+$ cells may be provided by infusion. The $CD34^+$ cells and/or $CD3^+$ cells may be provided in an inpatient procedure or in an outpatient procedure. An inpatient procedure requires admission to a hospital, and the patient may spend one or more nights in the hospital. An outpatient procedure does not require admission to a hospital and may be performed in a non-hospital setting, such as a clinic, doctor's office, home, or other location.

The compositions of the invention may be used in conjunction with transplantation of any solid organ. For example and without limitation, the solid organ may be a kidney, lung, pancreas, pancreatic, islet cells, heart, intestine, colon, liver, skin, muscle, gum, eye, or tooth. The transplant may include a complete organ, a portion of an organ, or cells from a tissue of an organ. The cellular product may be provided prior to, during, or subsequent to the solid organ transplant. For example and without limitation, the cellular product may be provided one, two, three, four, five, or six days or one, two, three, or four weeks prior to the solid organ transplant, or it may be provided one, two, three, four, five, or six days or one, two, three, or four weeks after the solid organ transplant.

To facilitate establishment of mixed chimerism in the recipient, the recipient's immune system may be conditioned in conjunction with providing the cellular product. For example, non-myeloablative conditioning may be used. In non-myeloablative conditioning, the recipient is exposed to drugs, antibodies, irradiation, or some combination thereof at a dose that is too low to eradicate all the bone marrow cells. Typically, the conditioning regimen includes treatment with anti-thymocyte globulin (ATG), total lymphoid irradiation, and corticosteroids (e.g. prednisone) for a period of from about 10 to 12 days (e.g. for about 11 days). The irradiation may be targeted to a particular location of the recipient's body. For example, irradiation may be targeted to a tissue, an organ, a region of the body or the whole body. Irradiation may be targeted to the lymph nodes, the spleen, or the thymus or any other area known to a person of skill in the art. When multiple doses of irradiation are administered, the doses may be targeted to the same location or to different locations. Non-myeloablative conditioning may include the use of a T cell depleting agent, such as a monoclonal antibody or drug, e.g., fludarabine. Regimens for non-myeloablative conditioning are known in the art and are described in, for example, U.S. Pat. No. 9,561,253, the contents of which are incorporated herein by reference.

The methods may include immunosuppressive therapy. Immunosuppressive therapy, or immunosuppression, involves treatment of the graft recipient with agents that diminish the response of the host immune system against the donor cells, which can lead to graft rejection. Primary immunosuppressive agents include calcineurin inhibitors, such as tacrolimus, cyclosporin A. Adjuvant agents are usually combined with a calcineurin inhibitor. Adjuvant agents include steroids, azathioprine, mycophenolic acid (MPA) agents, such as mycophenolate mofetil, mTOR inhibitors, such as sirolimus, and belatacept. The use of adjuvant agents allows clinicians to achieve adequate immunosuppression while decreasing the dose and toxicity of individual agents. Antibody-based therapy may use monoclonal (e.g., muromonab-CD3) or polyclonal antibodies or anti-CD25 antibodies (e.g., basiliximab, daclizumab). Antibody-based therapy allows for avoidance or dose reduction of calcineurin inhibitors, possibly reducing the risk of nephrotoxicity. Regimens for immunosuppressive therapy are known in the art and are described in, for example, U.S. Pat. No. 9,561,253, the contents of which are incorporated herein by reference.

Immunosuppression may also diminish the response of the donor immune cells against recipient tissue, which can lead to GVHD. GVHD may be acute or chronic. Acute GVHD typically occurs in the first 3 months after graft and may involve the skin, intestine, or the liver. Treatment for acute GVHD usually includes high-dose corticosteroids such as prednisone. Chronic GVHD typically occurs after the first 3 months following transplant and is the major source of late treatment-related complications. Chronic GVHD may cause functional disability and require prolonged immunosuppressive therapy.

Immunosuppressive therapy may occur in multiple phases. For example, the immunosuppressive regimen may have an induction phase and a maintenance phase. Induction and maintenance phase strategies may use different medicines at doses adjusted to achieve target therapeutic levels to enhance establishment of mixed chimerism in the recipient.

Immunosuppressive therapy may be withdrawn after stable mixed chimerism has been established in the recipient. The chimeric status of the recipient may be monitored as described below and deemed stable after a certain period, for example, 3 months, 6 months 12 months, 18 months, 24 months, or longer. Thus, immunosuppression may be discontinued for the recipients after a certain period, for example, 3 months, 6 months 12 months, 18 months, 24 months, or longer. Withdrawal of immunosuppressive therapy may include tapering, i.e., progressively reducing the dosage or frequency of treatment.

A determination of whether an individual is a full chimera, mixed chimera, or non-chimera made be made by an analysis of a hematopoietic cell sample from the solid organ transplant recipient, e.g. peripheral blood, bone marrow, etc. as known in the art. Analysis may be done by any convenient method of typing. Analysis may be performed on hematopoietic cells or a subset thereof, such as all mononuclear cells, T cells, B cells, $CD56^+NK$ cells, and $CD15^+$ neutrophils. Chimerism can be assessed by PCR analysis of microsatellites. For example, commercial kits that distinguish polymorphisms in short terminal repeat lengths of donor and host origin are available. Automated readers provide the percentage of donor type cells based on standard curves from artificial donor and host cell mixtures.

Recipients may be categorized as fully chimeric, mixed chimeric, or non-chimeric based on the fraction of cells that are derived from the donor. For example, recipients can be deemed fully chimeric if they have at least 90%, at least 95%, at least 98%, or at least 99% donor-derived cells. Recipients can be deemed mixed chimeric if they have too few donor-derived cells to be categorized as fully chimeric but a fraction of donor-derived cells that exceeds a certain threshold, such as at least 0.5%, at least 1%, at least 2%, at least 3%, at least 5%, at least 7.5%, at least 10% donor-derived cells. Recipients can be deem non-chimeric if the fraction of donor-derived cells falls below the threshold required to be categorized as mixed chimeric.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of manufacturing a cellular product for establishing mixed chimerism in a solid organ transplant recipient, the method comprising:
   receiving an apheresis product containing $CD34^+$ cells and $CD3^+$ cells from a solid organ transplant donor;
   dividing the apheresis product into a first portion and a second portion;
   purifying the first portion to obtain an enriched amount of $CD34^+$ cells;
   introducing from the second portion to the enriched amount of $CD34^+$ cells
   (i) the obtained $CD3^+$ cells in an amount greater than $1\times10^5$ $CD3^+$ cells/kg recipient weight and
   ii) circulating factors from blood of the donor, thereby creating a cellular product for establishing mixed chimerism in a solid organ transplant recipient.

2. The method of claim 1, wherein the first portion is column purified to obtain an enriched amount of $CD34^+$ cells.

3. The method of claim 1, wherein the $CD3^+$ cells and the circulating factors introduced to the enriched amount of $CD34^+$ cells are not column purified from the second portion.

4. The method of claim 1, wherein the cellular product comprises at least about $5\times10^5$ $CD34^+$ cells/kg recipient weight.

5. The method of claim 4, wherein the cellular product comprises at least about $4\times10^6$ $CD34^+$ cells/kg recipient weight.

6. The method of claim 1, wherein the cellular product comprises at least about $5\times10^5$ $CD3^+$ cells/kg recipient weight.

7. The method of claim 6, wherein the cellular product comprises at least about $5\times10^5$ $CD34^+$ cells/kg recipient weight.

8. The method of claim 6, wherein the cellular product comprises at least about $4\times10^6$ $CD34^+$ cells/kg recipient weight.

9. The method of claim 1, wherein the cellular product comprises at least about $5\times10^7$ $CD3^+$ cells/kg recipient weight.

10. The method of claim 9, wherein the cellular product comprises at least about $5\times10^5$ $CD34^+$ cells/kg recipient weight.

11. The method of claim 9, wherein the cellular product comprises at least about $4\times10^6$ $CD34^+$ cells/kg recipient weight.

12. The method of claim 1, wherein the donor comprises a Human Leukocyte Antigen (HLA) type that is matched to the recipient's HLA type.

13. The method of claim 12, wherein the donor and recipient are matched at alleles of each of HLA-A, HLA-B, HLA-C, HLA-DP, HLA-DQ, and HLA-DR genes.

14. The method of claim 1, wherein the donor comprises a HLA type that is mismatched to the recipient's HLA type.

15. The method of claim 14, wherein the donor and recipient are mismatched at at least one allele of a gene selected from the group consisting of HLA-A, HLA-B, HLA-C, HLA-DP, HLA-DQ, and HLA-DR genes.

16. The method of claim 1, wherein the cellular product comprises a cryoprotectant.

17. The method of claim 16, wherein the cryoprotectant comprises DMSO.

18. The method of claim 16, further comprising:
   cryopreserving the cellular product.

19. The method of claim 1, wherein the cellular product comprises a buffer.

20. The method of claim 19, wherein the cellular product is buffered to a pH of from about 6.0 to about 8.0.

* * * * *